United States Patent [19]

Ademovic

[11] Patent Number: 5,049,070
[45] Date of Patent: Sep. 17, 1991

[54] DENTAL DRILL INTEGRAL CAMERA AND OPTICS

[75] Inventor: Martin Ademovic, Soquel, Calif.

[73] Assignee: High-Tech Medical Instrumentation, Inc., San Francisco, Calif.

[21] Appl. No.: 462,678

[22] Filed: Jan. 9, 1990

[51] Int. Cl.⁵ .................. A61C 1/00; A61C 3/00; A61C 1/10; H04N 7/18

[52] U.S. Cl. ...................... 433/29; 433/114; 358/98

[58] Field of Search .............. 433/29, 114, 141

[56] References Cited

U.S. PATENT DOCUMENTS

| | | | |
|---|---|---|---|
| 4,403,956 | 9/1983 | Nakanishi | 433/29 |
| 4,727,416 | 2/1988 | Cooper et al. | 358/98 |
| 4,858,001 | 8/1989 | Milbank et al. | 358/98 |
| 4,917,603 | 4/1990 | Haack | 433/29 |

Primary Examiner—John J. Wilson
Assistant Examiner—Cindy A. Cherichetti
Attorney, Agent, or Firm—Townsend and Townsend

[57] ABSTRACT

A dental instrument (2) for use on a work area within a patient's mouth including controls for a tool element (16) illuminated by a fiber optic lens (46, 48) and displayed on a video imaging device (24). An elongated body (4) of the dental instrument houses connections (50) for communication between a control cable (18) and the distal end (15) of the instrument. Additionally, an objective element (20) and a camera (22) are sized to fit within the elongated body. The video imaging device monitors and/or records the work area via a light source (40), a video monitor system (42) and a video receiver (44). The elongated body includes an angled section (12) at the distal end of the body adjacent the tool element such that the fiber optic lens and video imaging device are oriented to illuminate the work area (26) within the patient's mouth. A quick-disconnect is provided for disconnecting the cable, connections and camera from the tool element.

25 Claims, 3 Drawing Sheets

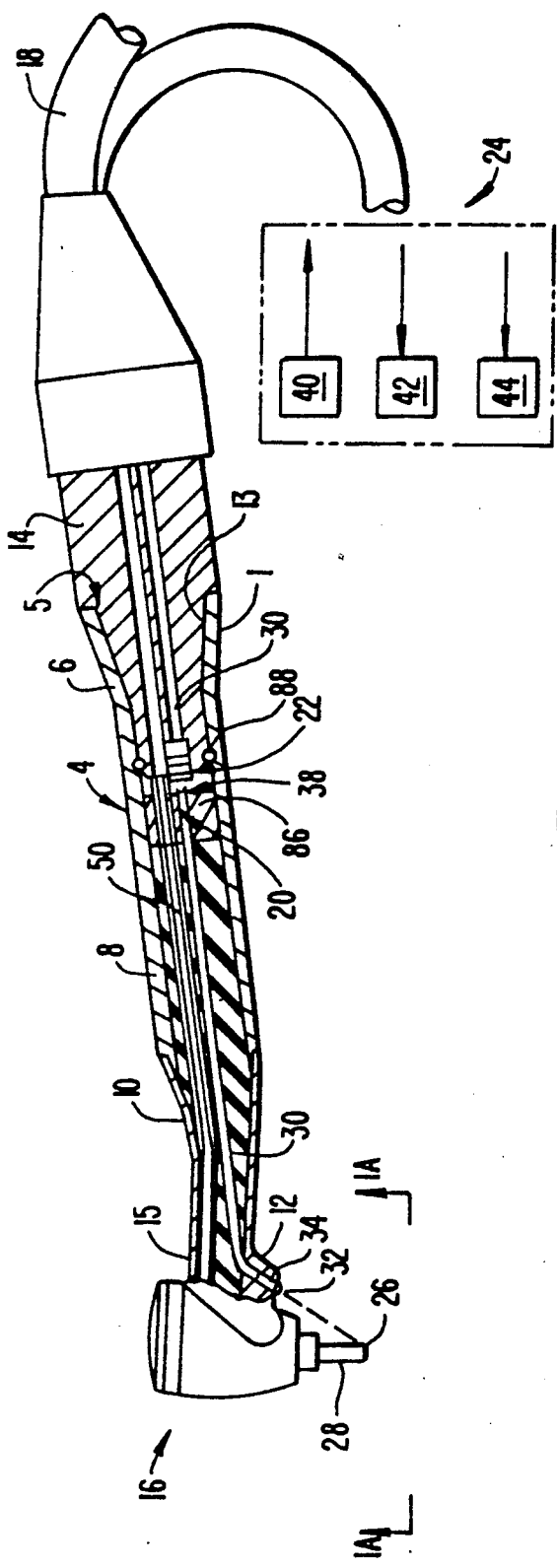
FIG._1.
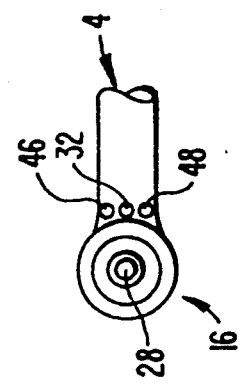
FIG._1A.

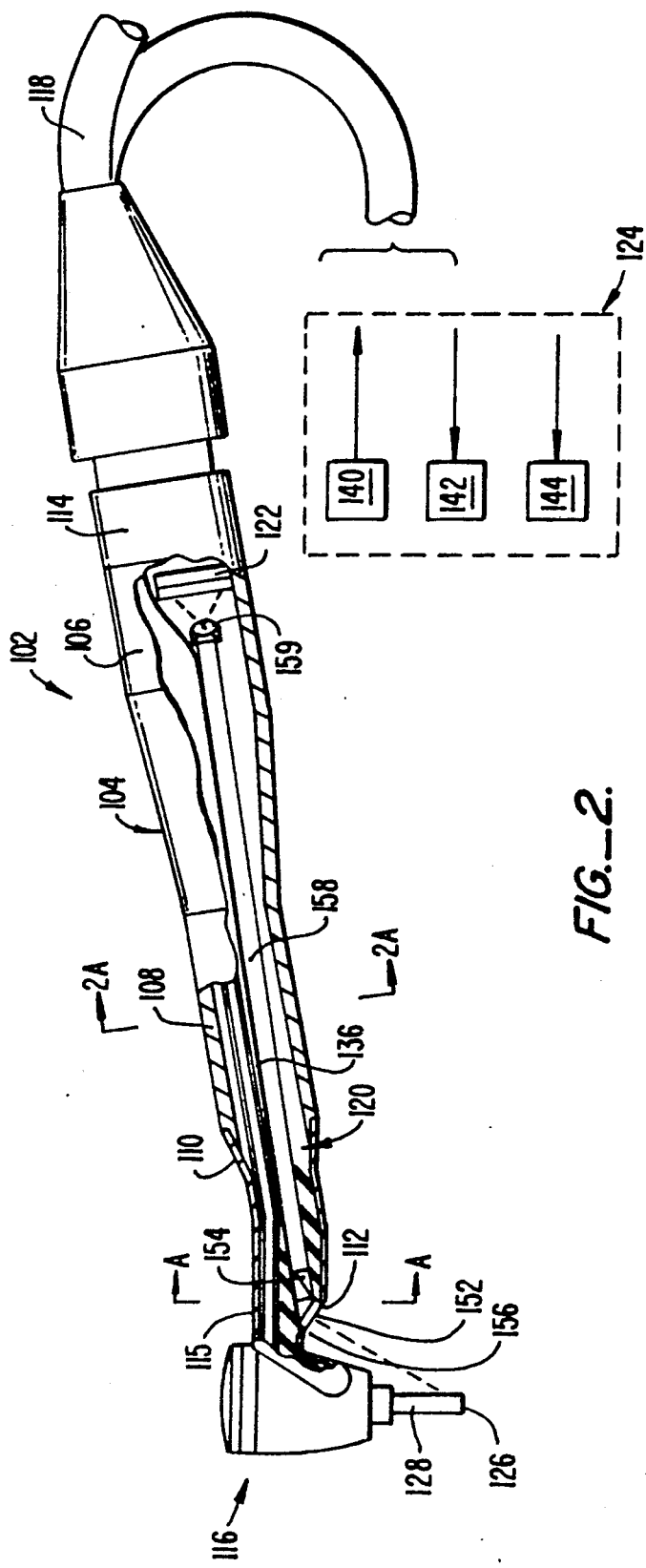
FIG._2.
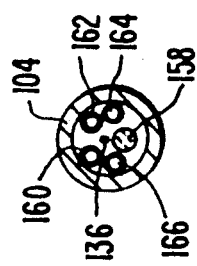
FIG._2A.

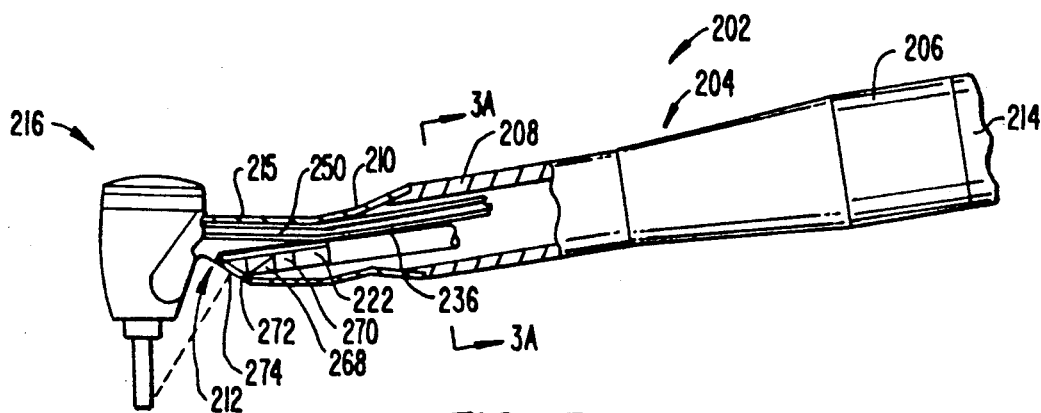
FIG._3.
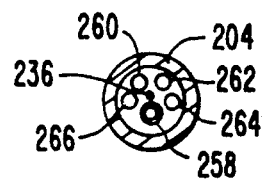
FIG._3A.
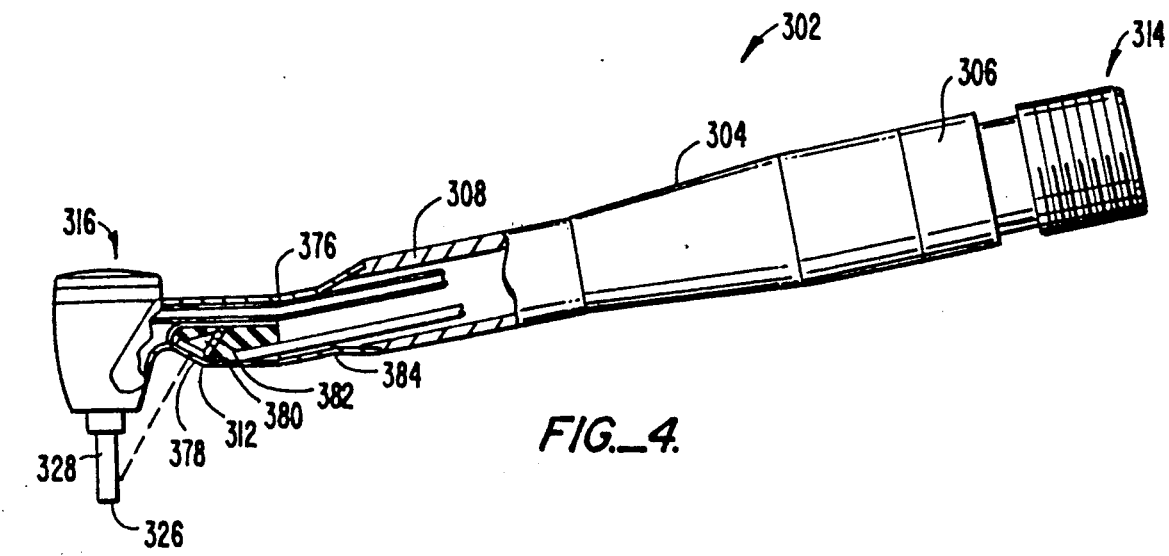
FIG._4.

DENTAL DRILL INTEGRAL CAMERA AND OPTICS

BACKGROUND OF THE INVENTION

The present invention relates to a dental instrument, in particular a dental drill, for use within a patient's mouth.

Preventive dentistry requires that cavities be filled. In so doing, the dentist must first determine that a cavity exists and locate it within the patient's mouth. Identification of a cavity is made after the patient notices a pain, through X-rays, or when the dentist views the patient's teeth during routine examination.

Dentists typically use a mirror to locate and view cavities, after which they are removed by drilling. Typically, a dentist uses a separate mirror to locate the cavity and removes it by employing a dental drill, placing the drill burr near the cavity. While drilling, the dentist often manipulates a separate mirror to provide a view for observing the progress of drilling and to ensure that the cavity is completely removed.

In the practice of dentistry, the X-ray machine has been the predominant imaging tool used to record and view dental and periodontal structure. Various improvements have been made in the field of dental instruments to assist the dentist in filling cavities. Hand held tools having mirrored surfaces provide visual access by the dentist to many, but not all areas of the mouth not directly viewable. One example is a dental mirror attached to the dental drill handpiece. This system allows the dentist to easily view the site at which drilling is being performed. However, a mirror mounted to the dental drill substantially limits access inside the mouth. This limited access occurs because the mirror protrudes from the drill, interfering with the other teeth, the gums, and the interior of the mouth. Such tools have the further limitation that they provide only a small image, and offer no capability to provide a permanent record of what the dentist sees.

The assignee of the present invention has developed an endoscope particularly adapted for use by dentists. The endoscope includes a camera capable of presenting an image for real-time viewing or for recording and playback at a later time. This design is the subject of U.S. Pat. No. 4,858,001 issued Aug. 15, 1989, which is incorporated by reference thereto. A dentist can view the interior of the mouth using the endoscope probe in conjunction with a video monitor. While suitable for locating cavities and diagnosing diseases and related ailments inside the mouth, it is difficult to use this device while drilling cavities or abrading portions of a tooth. In this respect, the endoscope exhibits the same disadvantages incurred in using a separate mirror, as discussed above. The dentist or dental assistant must hold the endoscope in one hand while trying to maneuver the dental drill with the other. Because both the drill and endoscope require connection to controls for their operation, it has not been feasible to combine an endoscope with a dental instrument in a size convenient for comfort and manipulation within a patient's mouth.

SUMMARY OF THE INVENTION

The present invention relates to a dental instrument integral with a light source and video imaging device allowing a dentist to view the work site within a patient's mouth while working therein. Only one instrument is required to both view the site and perform necessary operations.

The dental instrument includes an elongated body of conventional size for manipulating a dental tool. The elongated body additionally houses an objective element, a camera and a video imaging device. The dental tool is preferably a dental drill including a drill burr disposed at a distal end of the elongated body. The other, proximal end of the elongated body includes a handpiece for manipulating the dental instrument. The light source and objective element are oriented such that the tool and work site are both illuminated to permit examination through the video imaging device for real-time viewing or for recording and playback at a later time.

The objective element includes a lens or lenses, and a fiber optic bundle. The lens is preferably positioned on an angled section of the elongated body adjacent the distal end and oriented to capture the work site within the patient's mouth. Communication means, including lead wires and a fiber optic bundle, is housed within the elongated body for connecting the dental tool, the light source, and the video imaging device through a cable. The lens is connected to the camera via a fiber optic bundle. The camera, preferably a charge couple device (CCD) small-area image sensor, is housed within the elongated body. The preferred location is intermediate the distal and proximal ends of the elongated body, but it is within the scope of the present invention to place the camera at either end of the elongated body, i.e., adjacent the tool or the proximal end.

The cable for operation of the dental instrument is connected to the elongated body at its proximal end adjacent the handpiece. The cable is mounted externally to the handpiece and controls the video imaging device, as well as the light source.

In a preferred embodiment, the dental instrument includes a quick-disconnect such that the dental tool may be removed for sterilization, for example, by autoclaving. In this embodiment, the camera and communication means remains attached to the cable and need not be sterilized with the dental tool.

Other features and advantages will appear from the following description in which the preferred embodiments have been set forth in conjunction with the accompanying drawings.

BRIEF DESCRIPTION OF THE DRAWINGS

FIG. 1 illustrates a side view of the preferred embodiment of the present invention, partially cut away.

FIG. 1A illustrates a bottom view of the embodiment of FIG. 1 taken along lines 1—1.

FIG. 2 illustrates a side view of a second embodiment of the present invention, partially cut away.

FIG. 2A illustrates a cross-sectional view taken along lines 2—2 of FIG. 2.

FIG. 3 illustrates a side view of a third embodiment of the present invention, partially cut away.

FIG. 3A illustrates a cross-sectional view taken along lines 3—3 of FIG. 3.

FIG. 4 illustrates a fourth embodiment of the present invention.

DETAILED DESCRIPTION OF THE PREFERRED EMBODIMENTS

Referring now to the drawings, FIGS. 1-4 and 1A-3A illustrate various embodiments of dental drill 2 constructed in accordance with the present invention.

Dental drill 2, as seen in FIGS. 1 and 1A, includes an elongated body 4 having a handpiece 6 located at a first, proximal end 14 and a tool, in the preferred embodiment the tool is in the form of a drill head 16, disposed at a second, distal end 15 of elongated body 4. Objective element 20, camera 22 and video imaging device 24 allow a dentist to externally view work site 26 within a patient's mouth while performing operations with drill burr 28. A cable 18 is connected by a quick-disconnect (to be described below) to elongated body 4 at proximal end 14 for operation of dental drill 2 and video imaging device 24.

Elongated body 4 is composed of four basic contiguous sections, in consecutive order from proximal end 14 toward distal end 15: handpiece 6, a hollow central section 8, an intermediate section 10 and an angled section 12. Angled section 12 is disposed at distal end 15.

Drill head 16 is disposed adjacent distal end 15 of dental drill 2. Drill head 16 operates in a conventional manner, controlled by cable 18. Passageway member 50 provides air and water for drill head 16. Air is used to blow debris away from work site 26. Additionally, water is used to rinse the tooth area which has been recently drilled or abraded. As is conventional, many dental drills use an air turbine system for turning a small turbine within head 16. This turbine then rotates a collecting means (not shown) which holds burr 28 for abrading at high speed. A separate air passageway disposed within elongated body 4 provides a jet of air to the turbine. An air exhaust passageway exhausts the expended turbine air out and away from work site 26. The air turbine system is used to rotate drill burr 28. It is to be understood that other means, such as an electric motor mounted within elongated body 4 or a flexible drive shaft passing therethrough could be employed to rotate drill burr 28. Passageway member 50 will be more fully described below with reference to the embodiment of FIGS. 2 and 2A.

Camera 22 and objective element 20 are roughly cylindrical in shape, coaxial with each other, and housed within central section 8 in the assembled condition. Camera 22 is preferably a high-resolution, light sensitive charge coupled device (CCD) small-area image sensor of a type commercially available. In the preferred embodiment of FIGS. 1 and 1A, the camera employed is manufactured by Texas Instruments under model number TC210. Cameras other than CCD systems may also be successfully employed. Camera 22, as seen in FIG. 1, is disposed intermediate proximal end 14 and distal end 15 of elongated body 4. The image projected from drill burr 28 and work site 26 passes through an objective lens 32, a SELFOC lens 34 and a fiber optic bundle 36 to an imaging lens 38. Objective lens 32 is positioned on angled section 12 of elongated body 4 adjacent distal end 15 oriented so as to capture work site 26 within the patient's mouth. Imaging lens 38 projects the image of work site 26 onto camera 22. Camera 22 generates an electric signal representing the images transmitted through handpiece 6, by lead wires 30, to cable 18 and video imaging device 24. The signals are then converted to the appropriate signals for transmitting to a video monitor system 42.

Cable 18 is fixedly attached to proximal end 14. Handpiece 6 may be quick-disconnected from cable 18 at junction 5. Fiber optic bundle 36, passageway 50, and camera 22 remain coupled with cable 18. Handpiece 6, along with a supporting ring 86, are removed from cable 18 for sterilization. Supporting ring 86 maintains passageway 50 and fiber optic bundle 36 in its proper position. A tension ring and seal 88 in the form of an O-ring retains handpiece 6 and proximal end 14 in sealed relationship during use. Tension ring and seal 88 prevents drill head 16 from popping out of connection with proximal end 14. Handpiece 6 includes a tapered portion 7 cooperating with a tapered portion 13 of proximal end 14.

Video imaging device 24 includes a light source 40, video monitor system 42 and video receiver 44. Work site 26 is illuminated at lights 46, 48 (seen in FIG. 1A) by light source 40 transmitted through fiber optic bundle 36. Lights 46, 48 are disposed on angled section 12 and oriented so as to illuminate work site 26. An illuminated image of work site 26 is transmitted to camera 22 by way of objective element 20 and on to of video receiver 44 video imaging device 24 for immediate viewing, for recording and playback at a later time on a video recorder (not shown), or for both.

The operation of dental drill 2, which should be apparent from the above description, will now be described. The dentist or dental technician manipulates dental drill 2 by holding handpiece 6 so as to position drill head 16 within the patient's mouth such that drill burr 28 is disposed at work site 26, the location to be drilled. This procedure may be performed with video imaging device 24 functional, or by conventional means prior to operating video imaging device 24. Once drill head 16 is positioned and video imaging device 24 is operational, lights 46, 48 project a light beam of desired intensity to work area 26. Camera 22 and lights 46, 48 are controlled by video imaging device 24 via cable 18. Light source 40, disposed on angled section 12 of elongated body 4, illuminates work site 26 through fiber optic bundle 36. The image of work site 26 is projected through SELFOC lens 34, fiber optic bundle 36, and imaging lens 38 to camera 22, lead wires 30, and to video imaging device 24 for real time viewing or for recording and playback at a later time on video monitor system 42. Operation of drill head 16 is also controlled in a conventional manner through cable 18.

After use, drill head 16 is quick-disconnected from cable 18 and proximal end 14. Handpiece 6 is pulled from proximal end 14, releasing tension ring and seal 88. Supporting ring 86 and handpiece 6 are removed with drill head 16 for cleaning. Other portions of dental drill 2 remain coupled to cable 18. Drill head 16 may be sterilized by autoclaving and, thereafter, quick-connected to cable 18. Passageway 50, fiber optic bundle 36 and camera 22 are aligned. Tapered portions 7, 13 are forced into connection with each other to abut at junction 5. Tension ring and seal 88 retains dental drill 2 in its operational position.

FIGS. 2 and 2A disclose a modified form of a dental drill. Like reference numerals correspond to reference numerals of the embodiment of FIGS. 1 and 1A, incrementally increased by 100.

Camera 122 of the embodiment of FIGS. 2 and 2A differs from camera 22 of the embodiment of FIGS. 1 and 1A. Camera 122 is disposed at proximal end 114 of elongated body 104. Clear lens window 152 and related lens system 154 are positioned on angled section 112 for viewing drill burr 128 and work site 126. A fiber optic light 156 is disposed at distal end 115 of fiber optic bundle 136.

Fiber optic light lens 156 and fiber optic bundle 136 provide illumination for lens system 154 to pass an image through objective lens 158 mounted within elongated body 104 such that the desired image is then transmitted to lens 159 and camera 122. As in the embodiment described with reference to FIGS. 1 and 1A, the image from work site 126 is converted to electronic data signals which are then transmitted to video receiver 144 through cable 118. The electronic signals are then converted to the appropriate signals for transmitting to video monitor system 142. In the embodiment of FIGS. 2 and 2A, the camera employed is manufactured by Texas Instruments under model number TC211, although other cameras could be successfully employed.

FIG. 2A illustrates details of dental drill 102. Handpiece 106 includes various passageways employed in dental drill 102 which will now be described. Air passageway 160 supplies air for removing debris from work site 126. Similarly, a water passageway 162 is provided for rinsing work site 126 most recently drilled or abraded. Air inlet passageway 164 provides a jet of air to the turbine system, described above, while air exhaust passageway 166 is employed to exhaust expended turbine air out and away from work site 126.

The operation of the embodiment illustrated in FIGS. 2 and 2A is similar to the operation of the preferred embodiment of FIGS. 1 and 1A.

FIGS. 3 and 3A disclose a modified form of a dental drill. Like reference numerals correspond to reference numerals of the embodiment of FIGS. 1 and 1A, incrementally increased by 200.

Camera 222 of the embodiment of FIGS. 3 and 3A differs from camera 22 of the embodiment of FIGS. 1 and 1A. Camera 222 is disposed at distal end 215 of elongated body 204. Lens system 268 and lens 270 are positioned to provide the proper alignment and viewing angle for drilling, as discussed above. Clear lens window 272 is positioned to project the image of work site 226 through lens system 268. Lens 274 disposed on angled section 212, adjacent lens system 268 provides light through fiber optic bundle 236 to work site 226. A described with reference to the previously described embodiments, a light source (not shown) transmits light through fiber optic bundle 236 and elongated body 204 by a cable (not shown).

Operation of the embodiment of FIGS. 3 and 3A is similar to the operation of the previously described embodiments of FIGS. 1, 1A, 2 and 2A.

FIG. 4 discloses a modified form of a dental drill. Like reference numerals correspond to reference numerals of the embodiment of FIGS. 1 and 1A, incrementally increased by 300.

FIG. 4 includes a specially molded intermediate section 376 for receiving objective lens 378 and right angle prism 380, thereby optimizing the viewing angle and ease of assembly of lens 378 and prism 380 during manufacture. Drill burr 328 and work site 326 are projected through lens 378 and into prism 380. Work site 326 is reflected 90 degrees through prism 380, passing through prism-fiber optic joint 382 and fiber optic coherent bundle 384. The fiber optic camera CCD of FIG. 4 is identical to that of FIGS. 2 and 2A, described above.

This invention has been described with reference to the preferred embodiments. Variations and modifications can be made without departing from the scope of this invention which is limited only by the following claims. For example, the elongated body of the present invention could incorporate any convenient configuration. A camera other than a CCD could be successfully employed in this invention. A quick-disconnect could be employed in any of the alternate embodiments disclosed herein.

What is claimed is:

1. A dental drill comprising:
   an elongated body including a handpiece, said elongated body having a first end;
   a drill burr disposed at a work site located at said first end;
   means for illuminating said work site, said illumination means including a fiber optic bundle extending through said handpiece; and
   a video imaging device for displaying said work site at a location removed form said work site, said video imaging device being coupled to said illumination means and including a camera housed within said handpiece.

2. A dental drill comprising:
   a handpiece having a first end;
   a drill burr disposed at a work site located at said first end;
   light means disposed within said handpiece oriented such that said work site is adapted to be illuminated by said light means; and
   a video imaging device for displaying said work site at a location removed from said work site, said video imaging device comprising:
   a lens disposed at said first end;
   a camera housed within said handpiece;
   a light source, a video monitor system and a video receiver mounted external to said handpiece; and
   a cable mounted external to said handpiece for control of said light source, said video monitor system and said video receiver.

3. The dental drill as defined by claim 3 wherein said light means includes a fiber optic bundle extending through said handpiece.

4. The dental drill as defined by claim 2 further comprising communication means housed within said handpiece for connecting said drill burr, said light means and said video imaging device to said cable.

5. The dental drill as defined by claim 4 further comprising a quick-disconnect wherein said cable, said camera and said communication means remain coupled together and wherein said drill burr is disconnected.

6. The dental drill as defined by claim 3 wherein said camera is mounted intermediate said handpiece and spaced from said first end.

7. The dental drill as defined by claim 3 wherein said camera is mounted adjacent said first end of said handpiece.

8. The dental drill as defined by claim 3 wherein said camera is mounted at a second end of said handpiece opposite said first end.

9. The dental drill as defined by claim 3 wherein said elongated body includes an angled section disposed adjacent said first end and wherein said lens is positioned on said angled section.

10. The dental drill as defined by claim 3 further comprising a quick-disconnect wherein said camera and said cable remain coupled together and wherein said drill burr is disconnected.

11. A dental instrument for use on a work area within a patient's mouth, said instrument comprising:
    an elongated body having a hollow central region, a proximal end and a distal end;
    an objective element housed within said hollow central region for projecting the work area;

a camera housed within said elongated member for monitoring the work area;

a drill burr and a light means each disposed at said distal end;

an air passageway and a water passageway each extending through said elongated body and being in communication with said distal end; and a cable disposed on said elongated body for operation of said drill burr, said light means, said air passageway and said water passageway, said cable disposed at said proximal end and including communication means housed within said hollow central region for communicating with the work area at said distal end for operating said drill burr and said light means, for allowing air and water to reach said distal end through said air passageway and said water passageway, respectively, and for relaying the display from said camera to a location at the exterior of said elongated body.

12. The dental instrument as defined by claim 11 further comprising a video imaging device.

13. The dental instrument as defined by claim 12 wherein said elongated body includes an angled section disposed at said distal end and wherein said objective element comprises a lens positioned on said angled section.

14. The dental instrument as defined by claim 12 wherein said elongated body comprises a handpiece, said light means oriented such that said light means illuminates said work site.

15. The dental instrument as defined by claim 12 wherein said objective element comprises a lens disposed at said distal end;

said video imaging device comprising a video monitor system and a video receiver external to said elongated body; and said cable being mounted external to said elongated body for control of said video monitor system and said video receiver.

16. The dental instrument as defined by claim 11 wherein said objective element comprises a lens and a fiber optic bundle.

17. The dental instrument as defined by claim 11 wherein said camera is disposed in said hollow central region spaced from said distal end and from said proximal end.

18. The dental instrument as defined by claim 11 wherein said camera is disposed in said hollow central region adjacent said proximal end.

19. The dental instrument as defined by claim 11 wherein said camera is disposed adjacent said distal end.

20. The dental instrument as defined by claim 11 wherein said light means includes a fiber optic bundle extending through said elongated body.

21. The dental instrument as defined by claim 11 wherein said camera records the work area.

22. The dental instrument as defined by claim 11 further comprising a quick-disconnect for disconnecting said drill burr from said cable, said air passageway and, said water passageway.

23. The dental instrument as defined by claim 22 wherein said quick-disconnect comprises a tapered section formed on said proximal end cooperating with a tapered portion formed on said elongated body.

24. The dental instrument as defined by claim 23 further comprising a supporting ring for supporting said air passageway, said water passageway and said objective element.

25. The dental instrument as defined by claim 23 further comprising a ring for retaining said drill burr and said cable in an operational condition.

* * * * *